United States Patent [19]

Schmidt et al.

[11] 4,260,629

[45] Apr. 7, 1981

[54] TREATING PAIN WITH ACETAMINOPHEN AND 1,4-DIMETHYL-5-P-CHLOROBENZOYL-PYRROLE-2-ACETIC ACID

[75] Inventors: William K. Schmidt, Wilmington; Christine Smith, Newark; Dewey H. Smith, Jr., Wilmington; Vernon G. Vernier, Newark, all of Del.

[73] Assignee: E. I. Du Pont de Nemours and Company, Wilmington, Del.

[21] Appl. No.: 88,119

[22] Filed: Oct. 25, 1979

[51] Int. Cl.³ .................... A61K 31/40; A61K 31/165
[52] U.S. Cl. .................................... 424/274; 424/324
[58] Field of Search ............................... 424/274, 324

[56] References Cited

U.S. PATENT DOCUMENTS 4,132,788  1/1979  Wong .................................. 424/232

OTHER PUBLICATIONS

Castañer et al., "Drugs of the Future", vol. 2, pp. 698–701, (1977).
Merck Index, 9th Ed., (1976), p. 36.

*Primary Examiner*—Stanley J. Friedman

[57] ABSTRACT

Unexpectedly enhanced relief of pain in a mammal is obtained by oral administration of a composition consisting essentially of zomepirac or a pharmaceutically suitable salt thereof and acetaminophen.

6 Claims, 1 Drawing Figure

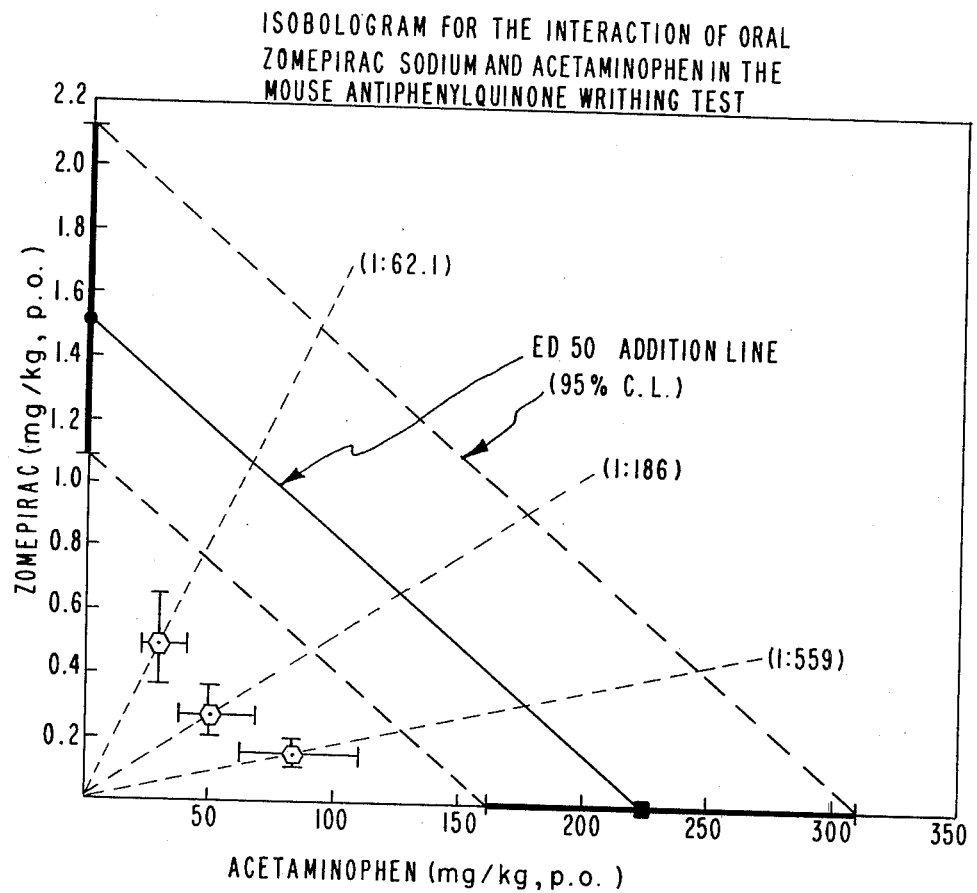

TREATING PAIN WITH ACETAMINOPHEN AND 1,4-DIMETHYL-5-P-CHLOROBENZOYL-PYRROLE-2-ACETIC ACID

BACKGROUND OF THE INVENTION

This invention relates to a method of relieving pain by using a pharmaceutical combinations of compounds having analgesic activity.

U.S. Pat. No. 3,752,826, issued to Carson on Aug. 14, 1973, discloses a class of anti-inflammatory 5-aroyl-pyrrole alkanoic acids. The compound 1,4-dimethyl-5-p-chlorobenzoyl-pyrrole-2-acetic acid, commonly known as zomepirac and having the formula

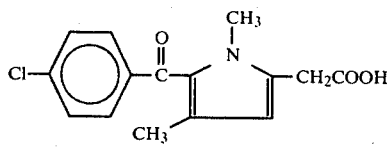

is specifically disclosed. J. Castañer and K. Hillier, "Drugs of the Future", vol. 2, pp. 698–701, 1977, disclose that zomepirac is an analgesic agent for the control of moderate to severe pain.

Acetaminophen, N-(4-hydroxyphenyl)acetamide, was first used in medicine by Van Mering in 1893, but only since 1949 has it gained in popularity as an effective alternative to aspirin for analgesic uses. Acetaminophen has been widely administered with a variety of other drugs, including opioid analgesics such as codeine, and antipyretic analgesics, such as aspirin. Goodman et al., "The Pharmacological Basis of Therapeutics", Fifth Ed., Macmillan Publishing Co., 1975, pp. 348–349, state that it is likely that an effective dose of an opioid or of an antipyretic analgesic such as aspirin will add to the analgesic effect of acetaminophen. A. W. Pircio et al., Arch. int. Pharmacodyn., 235, 116–123 (1978), however, have reported unexpectedly enhanced analgesic action with a 1:125 mixture of butorphanol,

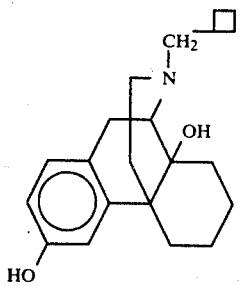

and acetaminophen; whereas a similar 1:10 combination did not show statistically-significant analgesic enhancement.

G. Stacher et al., Int. J. Clin. Pharmacol. Biopharmacy, 17, 250–255 (1979) report that coadministration of tolmetin,

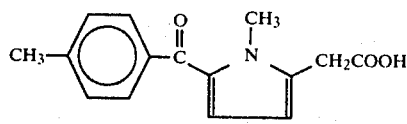

and acetaminophen permits a marked reduction of the dose of tolmetin needed to produce an analgesic effect in experimentally induced pain in human subjects. U.S. Pat. No. 4,132,788, issued to S. Wong on Jan. 2, 1979, discloses potentiation of the antiarthritic activity of 5-aroyl-1-(lower)alkylpyrrole-2-acetic acid derivatives by combination with aspirin or acetominophen. Antiarthritic potentiation with mixtures of tolmetin with acetaminophen and aspirin and zomepirac with acetaminophen and aspirin is specifically disclosed. The experimental procedures employed by Wong were not designed to detect pain, and furthermore, pain does not necessarily accompany inflammation or the development of arthritic disease in animals or in man.

Methods of relieving pain with analgesic combinations allowing reduced dosages are constantly being sought because thereby relief of pain can be obtained with a diminution of the expected side effects and toxicity which would result from the otherwise required higher dosages.

SUMMARY OF THE INVENTION

According to the present invention there is provided a method of alleviating pain in a mammal which comprises administering orally to said mammal an effective analgesic amount of a composition consisting essentially of zomepirac or a pharmaceutically suitable salt thereof and acetaminophen in a weight ratio of from about 1:10 to about 1:800.

BRIEF DESCRIPTION OF THE DRAWING

The drawing is a graph showing the interaction of zomepirac and acetaminophen on phenyl-p-benzoquinone induced writhing in mice.

DETAILED DESCRIPTION OF THE INVENTION

In the method of the invention zomepirac can be employed in the acid form or as a pharmaceutically suitable salt, such as those obtained from the appropriate organic or inorganic bases. The sodium salt is preferred because of its availability. In the method of the invention zomepirac or a pharmaceutically suitable salt thereof and acetaminophen are administered orally in a combination having a weight ratio of zomepirac to acetaminophen of from about 1:10 to about 1:800; preferably, from about 1:20 to about 1:700; and, most preferably, from about 1:40 to about 1:600. It has been found that when the combination of these compounds is administered in the aforestated ratios of components unexpectedly enhanced analgesic activity results, i.e., the resulting activity is greater than the activity expected from the sum of the activities of the individual components. In the method of the invention the highest analgesic activity is obtained by use of compositions within the most preferred range.

The method of the invention presents the opportunity of obtaining relief from pain with reduced dosages of zomepirac and acetaminophen, thereby diminishing the side effects and toxicity which would result from the otherwise required amounts of the individual drug components.

DOSAGE FORMS

In this discussion of dosage forms the term "active ingredient" is used to refer to the combination of zomepirac and acetaminophen. In the method of the invention the combination of analgesic agents can be administered orally to treat pain by any means that produces contact of the active ingredient with the ingredient's site or sites of action in the body of a mammal. The composition can be administered by any conventional means available for use in conjunction with pharmaceuticals. It can be administered alone, but is generally administered with a pharmaceutical carrier selected on the basis of the chosen route of administration and standard pharmaceutical practice.

In the method of the invention, the dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage can be such that the active ingredient is administered at a daily dosage of from about 0.4 to 4.2 milligrams per kilogram (mg/kg) of body weight of zomepirac and from about 10.8 to 54 mg/kg of acetaminophen. Ordinarily, administration of the composition in divided doses 2–5 times per day or in sustained release form is effective to obtain desired results.

In the present method, dosage forms (compositions) suitable for internal administration contain from about 50 milligrams to about 600 milligrams of active ingredient per unit. In these pharmaceutical compositions the active ingredient will ordinarily be present in an amount of about 0.5–95% by weight based on the total weight of the composition.

In the method of the invention, the active ingredient can be administered orally in solid dosage forms, such as capsules, tablets, and powders, or in liquid dosage forms, such as elixirs, syrups, and suspensions.

Gelatin capsules contain the active ingredient and powdered carriers, such as lactose, sucrose mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastro-intestinal tract. Liquid dosage forms for oral administration can contain coloring and flavoring to increase patient acceptance.

Suitable pharmaceutical carriers are described in *Remington's Pharmaceutical Sciences*, E. W. Martin, a standard reference text in this field.

Useful pharmaceutical dosage-forms for use in the method of the invention can be illustrated by the following examples:

EXAMPLE 1

| Zomepirac/Acetaminophen Tablets (3.75/325 mg) | |
|---|---|
| Formula (1:87) | mg/Tablet |
| Acetaminophen | 325.00 |
| Sucrose | 1.00 |
| Povidone | 8.00 |
| Purified Water | 10.00 |
| Modified Starch | 60.00 |
| Silica Gel | 11.00 |
| Sodium Zomepirac | 3.75 |
| Microcrystalline Cellulose | 266.25 |
| Stearic Acid | 15.00 |
| | 700.00 mg |

A large number of tablets can be prepared by conventional procedures, utilizing the formula above. The tablets can be used in the method of the invention to provide enhanced analgesic activity.

EXAMPLE 2

| Zomepirac/Acetaminophen Tablets (3.75/500 mg) | |
|---|---|
| Formula (1:133) | mg/Tablet |
| Acetaminophen | 500.00 |
| Sucrose | 2.00 |
| Povidone | 13.00 |
| Purified Water | 15.00 |
| Modified Starch | 45.00 |
| Silica Gel | 17.00 |
| Sodium Zomepirac | 3.75 |
| Microcrystalline Cellulose | 162.25 |
| Stearic Acid | 12.00 |
| | 770.00 mg |

A large number of tablets can be prepared by conventional procedures, utilizing the formula above. The tablets can be used in the method of the invention to provide enhanced analgesic activity.

EXAMPLE 3

Zomepirac/Acetaminophen Tablets
(a) Formula (1:32.5) (10/325 mg/Tablet)

| | mg/Tablet |
|---|---|
| Acetaminophen | 325.00 |
| Sucrose | 1.00 |
| Povidone | 8.00 |
| Purified Water | 10.00 |
| Modified Starch | 60.00 |
| Silica Gel | 11.00 |
| Sodium Zomepirac | 10.00 |
| Microcrystalline Cellulose | 260.00 |
| Stearic Acid | 15.00 |
| | 700.00 mg |

(b) Formula (1:13) (25/325 mg/Tablet)

| | mg/Tablet |
|---|---|
| Acetaminophen | 325.00 |
| Sucrose | 1.00 |
| Povidone | 8.00 |
| Purified Water | 10.00 |
| Modified Starch | 60.00 |
| Silica Gel | 11.00 |
| Sodium Zomepirac | 25.00 |
| Microcrystalline Cellulose | 245.00 |
| Stearic Acid | 15.00 |
| | 700.00 mg |

A large number of tablets can be prepared by conventional procedures, utilizing the formulas above. The tablets can be used in the method of the invention to provide enhanced analgesic activity.

EXAMPLE 4

Zomepirac/Acetaminophen Oral Liquid
(a) Formula (1:87) 3.75/325 mg/10 ml

|  | Amount/10 ml |
| --- | --- |
| Acetaminophen | 325.00 mg |
| Sodium Zomepirac | 3.75 mg |
| Propylene Glycol | 2.00 ml |
| Glycerin | 3.00 ml |
| Ethanol | 0.85 ml |
| Sorbitol Solution | 3.00 ml |
| Sodium Benzoate | 10.00 mg |
| Flavor | 0.01 ml |
| Purified Water | 10.00 ml |

(b) Formula (1:32.5) 10/325 mg/10 ml

|  | Amount/10 ml |
| --- | --- |
| Acetaminophen | 325.00 mg |
| Sodium Zomepirac | 10.00 mg |
| Propylene Glycol | 2.00 ml |
| Glycerin | 3.00 ml |
| Ethanol | 0.85 ml |
| Sorbitol Solution | 3.00 ml |
| Sodium Benzoate | 10.00 mg |
| Flavor | 0.01 ml |
| Purified Water | 10.00 ml |

(c) Formula (1:13) 25/325 mg/10 ml

|  | Amount/10 ml |
| --- | --- |
| Acetaminophen | 325.00 mg |
| Sodium Zomepirac | 25.00 mg |
| Propylene Glycol | 2.00 ml |
| Glycerin | 3.00 ml |
| Ethanol | 0.85 ml |
| Sorbitol Solution | 3.00 ml |
| Sodium Benzoate | 10.00 mg |
| Flavor | 0.01 ml |
| Purified Water | 10.00 ml |

An oral liquid can be prepared by conventional methods, utilizing the formulas above. The oral liquid can be used in the method of the invention to provide enhanced analgesic activity.

EXAMPLE 5

Zomepirac/Acetaminophen Capsules
(a) Formula (1:87) 3.75/325 mg/CAP

|  | mg/CAP |
| --- | --- |
| Acetaminophen | 325.00 |
| Sodium Zomepirac | 3.75 |
| Modified Starch | 99.65 |
| Silicon Dioxide | 0.60 |
| Starch | 6.00 |
|  | 435.00 |

(b) Formula (1:32.5) 10/325 mg/CAP

|  | mg/CAP |
| --- | --- |
| Acetaminophen | 325.00 |
| Sodium Zomepirac | 10.00 |
| Modified Starch | 93.40 |
| Silicon Dioxide | 0.60 |
| Starch | 6.00 |
|  | 435.00 |

Zomepirac/Acetaminophen Capsules
(c) Formula (1:13) 25/325 mg/CAP

|  | mg/CAP |
| --- | --- |
| Acetaminophen | 325.00 |
| Sodium Zomepirac | 25.00 |
| Modified Starch | 78.40 |
| Silicon Dioxide | 0.60 |
| Starch | 6.00 |
|  | 435.00 |

A large number of unit capsules can be prepared by filling standard two-piece hard gelatin capsules with the above formulas utilizing conventional techniques. The capsules can be used in the method of the invention to provide enhanced analgesic activity.

UTILITY

Test Methods

The unexpectedly enhanced analgesic activity obtained in the method of the invention is evidenced by tests conducted on mice. Male $CF_1$ mice obtained from Charles River Breeding Laboratories, fasted for 16–22 hours, and weighing 18–22 g at the time of testing are used throughout. All mice are dosed orally with acetaminophen and/or zomepirac (calculated as the sodium salt) dissolved completely in distilled water containing as vehicle 2% by volume of Tween 80 ®, a pharmacological dispersant manufactured by Fisher Scientific Company and containing 100% polysorbate 80. A dosing volume of 20 ml/kg is used. All doses are coded and the test is performed under a code not known to the observer.

ANALGESIC ACTIVITY IN THE MOUSE ANTIPHENYLQUINONE WRITHING TEST

A standard procedure for detecting and comparing the analgesic activity of different classes of analgesia drugs for which there is a good correlation with human efficacy is the prevention of phenyl-p-benzoquinone induced writhing in mice (H. Blumberg et al.; Proc. Soc. Exp. Biol. Med. 118, 763–766, 1965).

Mice, intubated with various doses of sodium zomepirac, acetaminophen, combined doses of sodium zomepirac and acetaminophen, or vehicle, are injected intraperitoneally with a challenge dose of phenyl-p-benzoquinone. The phenyl-p-benzoquinone is prepared as a 0.1 mg/ml solution in 5% by volume of ethanol in water; the writhing dose is 1.25 mg/kg injected at the rate of 0.25 ml/20 g. For scoring purposes a "writhe" is indicated by whole body stretching or contraction of the abdomen: mice are observed 10 minutes for the presence or absence of writhing beginning 5 minutes after receiving the phenyl-p-benzoquinone dose. Each mouse is used only once, then discarded.

All ED50 values are determined numerically by the moving average method of Thompson (W. F. Thompson: Bacteriological Rev. 11, 115–145, 1947) and 95% confidence limits are calculated according to the method of Litchfield and Wilcoxon (J. T. Litchfield, Jr. and F. Wilcoxon: J. Pharm. Exp. Ther. 96, 99–113, 1949). As used herein ED50 means the dosage at which 50% of the mice in a test group exhibit an analgesic response.

In a preliminary experiment the oral analgesic values (ED50's) at 10 minutes were 1.16 mg/kg for sodium zomepirac and 216 mg/kg for acetaminophen with 95% confidence limits being 0.80–1.69 mg/kg and 166–281 mg/kg, respectively. In order to study the interaction between zomepirac and acetaminophen, precise dosage ratios of sodium zomepirac and acetaminophen are selected. Four to five coded doses of each selected combination are studied for analgesic effectiveness at 10 minutes using an experimental design which permits complete randomization of the separate dosage forms tested. Altogether 25 separate dosage forms are used and each form is represented in each experimental session. The experiments are continued by running experimental sessions with an equal number of mice being tested for each dosage group until the total number, N, of mice tested per group is 20.

The interaction of sodium zomepirac and acetaminophen on phenyl-p-benzoquinone induced writhing in mice is demonstrated by the data in the Table and in the Loewe isobologram (S. Loewe: *Pharm. Rev.* 9: 237–242, 1957) in the drawing. In the drawing, the diagonal line joining the ED50 values of the two drugs given separately represents simple additivity of drug effects. The dashed lines on each side of the diagonal line give the 95% confidence limits for this line of additivity. ED50's falling under the curve (between the line and the origin) indicate potentiation (unexpected enhancement) of effects while those outside of the curve would suggest antagonism between the two drugs. The 3 diagonal lines radiating from the origin represent the dose ratios of sodium zomepirac to acetaminophen used in mice receiving the combined drug dosages. The horizontal and vertical bars through each ED50 point are the 95% confidence limits. The drawing shows that in the method of the invention compositions having a ratio of sodium zomepirac to acetaminophen from 1:10 to 1:800 give unexpectedly enhanced activity since the 95% confidence limits of the ED50 values for those ratios do not overlap the line of additivity.

TABLE

ORAL SODIUM ZOMEPIRAC/ACETAMINOPHEN COMBINATIONS IN THE MOUSE ANTIPHENYLQUINONE WRITHING TEST
(N = 20 Mice/Dose)

| DRUG COMBINATIONS ZOMEPIRAC . Na: Acetaminophen | DRUG DOSE (mg/kg) Sodium Zomepirac | Acetaminophen | % MICE BLOCKED | ED50 at 10 Min. (95% Confidence limits) Sodium Zomepirac | Acetaminophen |
|---|---|---|---|---|---|
| (Control Solvents) | 0 | 0 | 0% | — | — |
|  | 0.29 | 0 | 5% | 1.52 mg/kg | — |
| (Sodium Zomepirac only) | 0.58 | 0 | 20% | (1.09–2.12) |  |
|  | 1.16 | 0 | 35% |  |  |
|  | 2.32 | 0 | 60% |  |  |
|  | 4.64 | 0 | 95% |  |  |
|  | 0.218 | 13.5 | 5% |  |  |
|  | 0.435 | 27. | 40% |  |  |
| 1:62.1 | 0.87 | 54. | 90% | 0.488 mg/kg | 30.3 mg/kg |
|  | 1.74 | 108. | 95% | (0.367– | (22.6– |
|  | 3.48 | 216. | 100% | 0.649) | 40.6) |
|  | 0.145 | 27. | 5% |  |  |
|  | 0.29 | 54. | 60% | 0.273 mg/kg | 50.8 mg/kg |
| 1:186 | 0.58 | 108. | 90% | (0.204– | (37.7– |
|  | 1.16 | 216. | 90% | 0.365) | 68.5) |
|  | 2.32 | 432. | 100% |  |  |
|  | 0.073 | 40.5 | 25% |  |  |
|  | 0.145 | 81. | 40% |  |  |
| 1:559 | 0.29 | 162. | 90% | 0.149 mg/kg | 83.2 mg/kg |
|  | 0.58 | 324. | 95% | (0.114– | (62.6–111) |
|  | 1.16 | 648. | 100% | 0.195) |  |
|  | 0 | 54. | 10% |  |  |
| (Acetaminophen only) | 0 | 108. | 30% |  |  |
|  | 0 | 216. | 45% | — | 224 mg/kg |
|  | 0 | 432. | 75% |  | (162–309) |

What is claimed is:

1. A method of alleviating pain in a mammal which comprises administering orally to said mammal an effective analgesic amount of a composition consisting essentially of zomepirac or a pharmaceutically suitable salt thereof and acetaminophen in a weight ratio of from about 1:10 to about 1:800.

2. A method according to claim 1 wherein the weight ratio is from about 1:20 to about 1:700.

3. A method according to claim 1 wherein the ratio is from about 1:40 to about 1:600.

4. A method according to claim 1 wherein zomepirac is present in the composition as the sodium salt.

5. A method according to claim 2 wherein zomepirac is present in the composition as the sodium salt.

6. A method according to claim 3 wherein zomepirac is present in the composition as the sodium salt.

* * * * *